United States Patent [19]

Evans et al.

[11] 4,131,682

[45] Dec. 26, 1978

[54] HETEROARYL KETONE DERIVATIVES

[75] Inventors: Delme Evans, Chalfont St. Peter; John C. Saunders, Maidenhead; William R. N. Williamson, Slough, all of England

[73] Assignee: Lilly Industries Limited, London, England

[21] Appl. No.: 840,883

[22] Filed: Oct. 11, 1977

[30] Foreign Application Priority Data

Oct. 14, 1976 [GB] United Kingdom ............... 42684/76

[51] Int. Cl.² .................... C07D 333/10; A61K 31/38
[52] U.S. Cl. ............................. 424/275; 260/326.5 J; 260/332.3 R
[58] Field of Search ................... 260/326.5 J, 332.3 R; 424/275

[56] References Cited

U.S. PATENT DOCUMENTS 4,000,160  12/1976  Bailey ............................. 260/326.5 J

OTHER PUBLICATIONS

Prakash et al., Chemical Abstracts, vol. 77, 101317d, (1972).
Birchall et al., Chemical Abstracts, vol. 74, 141434d, (1971).
Prakash et al., Def. Sci. J., 21(2), 143–148, (1971).
Derwent Abstract, 06275x/04, (1974).
Derwent Abstract, 52804w/32, (1974).

Primary Examiner—Jose Tovar
Attorney, Agent, or Firm—Kathleen R. S. Page; Arthur R. Whale

[57] ABSTRACT

Novel heteroaryl ketone derivatives, specifically a class of phenyl heteroaryl methanone derivatives, having anti-allergy activity, pharmaceutical formulations containing diphenylmethane derivatives and methods of treatment utilizing such derivatives.

7 Claims, No Drawings

HETEROARYL KETONE DERIVATIVES

This invention relates to a class of novel heteroaryl ketone derivatives, to methods of preparing such derivatives, and to pharmaceutical formulations.

(2-Hydroxy-5-methylphenyl)(2-thienyl)methanone has been described by Prakash et al in Def.Sci.J., 1971,21(2),143-8 (C.A., 77, 101317d). However no utility, and in particular no pharmacological activity, is described therein.

According to the present invention there is provided a heteroaryl ketone derivative of formula (I):

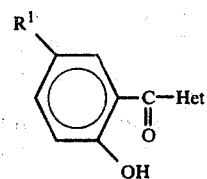

wherein $R^1$ is $C_{1-4}$ alkyl and Het is thienyl or pyrrolyl optionally substituted by up to three groups selected from halogen and $C_{1-4}$ alkyl, or a pharmaceutically acceptable salt thereof, provided that when Het is 2-thienyl, $R^1$ is $C_{2-4}$ alkyl.

The invention also provides a pharmaceutical formulation comprising an active ingredient in association with a pharmaceutically acceptable carrier therefor, the active ingredient being a compound of formula (I) as defined above or (2-hydroxy-5-methylphenyl)(2-thienyl)methanone; and a method of making such a pharmaceutical formulation which comprises bringing a compound of formula (I) as defined above or (2-hydroxy-5-methylphenyl) (2-thienyl)methanone into association with a pharmaceutically acceptable carrier therefor.

In accordance with the invention, there is further provided a method of treating an animal suffering from or susceptible to an allergic condition, and particularly a method of treating immediate hypersensitivity diseases such as asthma in animals, including humans, which method comprises administering to the animal a therapeutically effective amount of a compound of formula (I) as defined above or (2-hydroxy-5-methlyphenyl) (2-thienyl)methanone.

Preferred compounds of formula (I) are those having one or more of the following features:
(a) $R^1$ is $C_{2-4}$ alkyl,
(b) $R^1$ is ethyl,
(c) Het is thienyl optionally substituted by halogen or methyl,
(d) Het is 2-thienyl optionally substituted by halogen or methyl,
(e) Het is 2-thienyl,
(f) Het is 5-methyl-2-thienyl,
(g) Het is 5-chloro-2-thienyl,
(h) Het is 3-thienyl,
(i) Het is pyrrolyl optionally substituted by halogen or methyl,
(j) Het is 2-(N-methyl)pyrrolyl.

Particularly preferred compounds are those having features (a) and (e), (a) and (f), (a) and (g) and (a) and (j), and more especially preferred are those compounds having features (b) and (e), (b) and (f), (b) and (g) and (b) and (j).

The present invention also provides a method of preparing a compound of formula (I) as defined above comprising
(i) reacting a compound of formula:

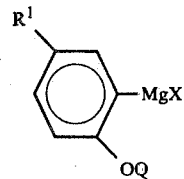

wherein $R^1$ is $C_{1-4}$ alkyl, Q is $C_{1-4}$ alkyl or $C_{2-5}$ acyl, and X is halogen, with a compound of formula:

wherein Het is as defined above, and hydrolysing and resulting organometallic product, preferably with an acid,
(ii) treating a compound of formula:

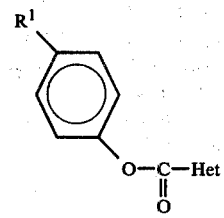

wherein $R^1$ and Het are as defined above, with a Lewis acid, such as $AlCl_3$, and hydrolysing the resulting complex, or
(iii) reacting a compound of formula:

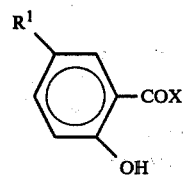

where $R^1$ is $C_{1-4}$ alkyl and X is halogen with a compound of formula:

where Het is as defined above with a Lewis acid, for example Al $Cl_3$, and hydrolysing the resulting complex.

It will readily be appreciated those skilled in the art that step (i) above is reaction between a Grignard reagent and an appropriate heteronitrile compound and may be carried out under conventional reaction conditions. Similarly, step (ii) is a Fries rearrangement and step (iii) is Friedel-Crafts acylation, both of which reactions may be carried out under conventional reaction conditions.

The heteroaryl ketone derivatives of the present invention are useful in the prophylactic treatment of immediate hypersensitivity conditions including asthma and in the alleviation of status asthmaticus in humans. The compounds have low toxicity.

The compounds or compositions of the present invention may be administered by various routes and for this purpose may be formulated in a variety of forms.

Thus the compounds or compositions may be administered by the oral and rectal routes, topically, parenterally, e.g. by injection and by continuous or discontinuous intra-arterial infusion, in the form of, for example, tablets, lozenges, sub-lingual tablets, sachets, cachets, elixirs, suspensions, aerosols, ointments, for example containing from 1 to 10% by weight of the active compound in a suitable base, soft and hard gelatin capsules, suppositories, injection solutions and suspensions in physiologically acceptable media, and sterile packaged powders absorbed onto a support material for making injection solutions. Advantageously for this purpose, compositions may be provided in dosage unit form, preferably each dosage unit form, preferably each dosage unit containing from 5 to 500 mg. (from 5.0 to 50 mg. in the case of parenteral administration, from 5.0 to 50 mg. in the case of inhalation and from 25 to 500 mg. in the case of oral or rectal administration) of a compound of formula (I).

Dosages of from 0.5 to 85 mg/kg per day, preferably 2 to 20 mg/kg, of active ingredient may be administered. It will however readily be understood that the amount of the compound or compounds of formula (I) actually to be administered will be determined by a physician, in the light of all the relevant circumstances including the condition to be treated, the choice of compound to be administered and the choise of route of administration and therefore the above preferred dosage range is not intended to limit the scope of the present invention in any way.

In this specification, the expression "dosage unit form" is used as meaning a physically discrete unit containing an individual quantity of the active ingredient, generally in admixture with a pharmaceutical diluent therefor, or otherwise in association with a pharmaceutical carrier, the quantity of the active ingredient being such that one or more units are normally required for a single therapeutic administration or that, in the case of severable units such as scored tablets, at least one fraction such as a half or a quarter of a severable unit is required for a single therapeutic administration.

The formulations of the present invention normally will consist of at least one compound of formula (I) associated with a pharmaceutically acceptable carrier therefor, i.e. mixed with a carrier, or diluted by a carrier, or enclosed or encapsulated by an ingestible carrier in the form of a capsule, sachet, cachet, paper or other container or by a disposable container such as an ampoule. A carrier or diluent may be a solid, semisolid or liquid material, which serves as a vehicle, excipient or medium for the active therapeutic substance.

Some examples of the diluents or carriers which may be employed in the pharmaceutical compositions of the present invention are lactose, dextrose, sucrose, sorbitol, mannitol, propylene glycol, liquid paraffin, white soft paraffin, kaolin, fumed silicon dioxide, microcrystalline cellulose, calcium silicate, silica, polyvinylpyrrolidone, cetostearyl alcohol, starch, modified starches, gum acacia, calcium phosphate, cocoa butter, ethoxylated esters, oil of theobroma, arachis oil, alginates, tragacanth, gelatin, syrup B.P., methyl cellulose, polyoxyethylene sorbitan monolaurate, ethyl lactate, methyl and propyl hydroxybenzoate, sorbitan trioleate, sorbitan sesquioleate and oleyl alcohol and propellants such as trichloromonofluoromethane, dichlorodifluoromethane and dichlorotetrafluoroethane. In the case of tablets, a lubricant may be incorporated to prevent sticking and binding of the powdered ingredients in the dies and on the punch of the tabletting machine. For such purpose there may be employed for instance aluminum, magnesium or calcium stearates, talc or mineral oil.

The invention will be further understood from the following Examples:

EXAMPLE 1.

(2-Hydroxy-5-ethylphenyl)(2-thienyl)methanone

2-Hydroxy-5-ethylbenzoic acid (16.6g, 0.1 mol) and thionyl chloride (12.44g, 0.105 mol) were mixed together with light petroleum (bp 40°–60° C.) (75 ml) and pyridine (0.1 ml) and refluxed for 6 hours. The resulting 2-hydroxy-5-ethylbenzoyl chloride was stirred in carbon disulphide (120 ml), cooled in ice and treated with aluminium chloride for 1 to 2 minutes. The temperature of the mixture rose from 2° C. to 15° C. The temperature was allowed to return to about 2° C. and thiophene (8.4g, 7.91 ml. 0.1 mol) in carbon disulphide (25 ml) was added at a rate such that the temperature of the mixture did not rise above about 3° C. The mixture was then stirred at room temperature overnight, stirred and refluxed for 3½ hours, cooled, poured into ice and concentrated hydrochloric acid, and extracted with ether. The ether fraction was washed firstly with a saturated solution of sodium bicarbonate and secondly with a saturated solution of sodium chloride, was dried (over $Na_2SO_4$), filtered and evaporated to yield an oil which was distilled to give the pure title product (0.67g), bp 118°–122° C./0.07 mm, $n_D^{19}$ 1.6280.

EXAMPLE 2

(2-Hydroxy-5-ethylphenyl)(5-methyl-2-thienyl)methanone

2-Hydroxy-5-ethylbenzoyl chloride (6.08g, 0.036 mol) and 2-methylthiophene were mixed together in tetrachloroethane (20 ml), and stannic chloride (18.78g, 0.072 mol) in tetrachloroethane (20 ml) was added dropwise with stirring, the temperature of the mixture being at about 20° C. by cooling with an ice bath. The mixture was then stirred at room temperature for 3 hours and left to stand at room temperature overnight. The resulting pink solution was poured into ice and concentrated hydrochloric acid (10 to 20 ml), stirred until the ice had melted and extracted with chloroform. The chloroform extract was washed firstly with a saturated solution of sodium bicarbonate and secondly with a saturated solution of sodium chloride, was dried (over $Na_2SO_4$), filtered and evaporated to leave an oil which distilled to give the pure title product (4.36g), bp 133°–136° C./0.1 mm, $n_D^{21}$ 1.6341.

EXAMPLE 3

(2-Hydroxy-5-ethylphenyl)(5-chloro-2-thienyl)methanone

This compound was prepared from 2-chlorothiophene using the method of Example 2 and had bp 136°–138° C./0.14 mm, $n_D^{23}$ 1.6484.

EXAMPLE 4

(2-Hydroxy-5-ethylphenyl)(3-thienyl)methanone (a) 4-Ethylphenylthiophene-3-carboxylate Thiophene-3-carboxylic acid (7.7g, 0.06 mol) was reluxed with $SOCl_2$ (13.1 ml) for 2 hours. The solution was evaporated to dryness to give the acid chloride (I.R (Nujol) 1750 $cm^{-1}$). This was treated with p-ethylphenol (7.35g, 0.06 mol) and pyridine (40 ml) and heated at 100° C. for 3 hours. The pyridine was evaporated off under reduced pressure, and the residue was treated with ice and hydrochloric acid and extracted with chloroform. The chloroform extract was washed with saturated NaHCO$_3$ solution, dried over Mg SO$_4$, filtered and evaporated to leave an oil which was distilled to give the ester, 4-ethylphenylthiophene-3-carboxylate bp 136°-138° C./1.2 mm, mp 65° C. Analysis: Found: C:67.1; H:5.27; S:14.27 C$_{13}$ H$_{12}$ O$_2$S requires C:67.21; H:5.21; S:13.8%.

(b) (2-Hydroxy-5-ethylphenyl)(3-thienyl)methanone

The above ester (8.72g, 0.037 mol) was mixed with AlCl$_3$ (7.09g, 0.053 mol) and stirred and heated in an oil bath at 140°-150° C. for 35 min. The mixture was allowed to cool and was treated with ice and concentrated hydrochloric acid and stirred until it reached room temperature. The product was extracted with chloroform, and the chloroform extract was washed with saturated NaH CO$_3$ solution and saturated NaCl solution, dried over MgSO$_4$ filtered and evaporated to give an oil (7.3g). This was dissolved in ethanol (250 ml), 2N NaOH (73 ml) was added and the mixture refluxed for 4 hours to remove contaminating ester. The resulting mixture was evaporated to dryness to leave a yellow solid, which was dissolved in water and acidified to give a yellow oil. This oil was extracted with ether. The ether extract was washed with saturated NaH CO$_3$ solution, saturated NaCl, dried over Na$_2$ SO$_4$ filtered and evaporated to give an oil which was distilled to give the title compound, bp.131°-133° C./0.4 mm (5.28g). Analysis: Found: C:67.23; H:5.01; S:14.02. C$_{13}$H$_{12}$O$_2$S requires C:67.21; H:5.21; S:13.8%

EXAMPLE 5.

(2-Hydroxy-5-ethylphenyl[2-(N-methyl)pyrrolyl]methanone.

N-Methlpyrrole (6.4g, 0.078 mol) in ether (40 ml) was cooled to −30° C. and treated with a suspension of 2-hydroxy-5-ethylbenzoyl chloride which was prepared as in Example 1 from 6.6g (0.039 mol) of the corresponding acid, in ether (200 ml). The addition rate and cooling were co-ordinated to keep the temperature at −30° C. to −25° C. The slightly brown mixture was stirred for 2 hours without external cooling until it reached 22° C. The brown solution was washed with saturated NaCl and NaH CO$_3$ solutions and again with NaCl solution, and dried over Mg SO$_4$, and the solvent was evaporated off to yield a brown oil which gave the title compound after purification by preparative thin layer chromatography using chloroform as eluent. Refractive index, n$_D^{23}$ 1.6231. Analysis: Found: C:73.06; H:6.41; N:6.02% C$_{14}$H$_{15}$NO$_2$ requires C:73.34; H:6.59; H:6.11%.

We claim:

1. A heteroaryl ketone derivative of formula

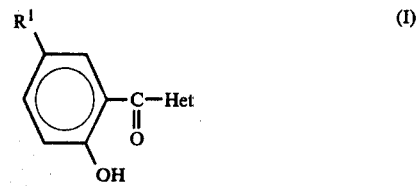

(I)

wherein R$^1$ is C$_{1-4}$ alkyl and Het is a heteroaryl group selected from thienyl and thienyl substituted by from one to three groups selected from halogen and C$_{1-4}$ alkyl, or a pharmaceutically acceptable salt thereof, provided that when Het is 2-thienyl, R$^1$ is C$_{2-4}$ alkyl.

2. The compound of claim 1 wherein R$^1$ is C$_{2-4}$ alkyl.

3. The compound of claim 2 wherein R$^1$ is ethyl.

4. The compound of claim 2 wherein Het is selected from thienyl, halothienyl, and methylthienyl.

5. The compound of claim 3 wherein Het is 2-thienyl.

6. A pharmaceutical formulation consisting essentially of a therapeutically effectaive amount of an active ingredient being a compound of formula (I)

(I)

where R$^1$ is C$_{1-4}$ alkyl and Het is a heteroaryl group selected from thienyl and thienyl substituted by from one to three groups selected from halogen and C$_{1-4}$ alkyl, or a pharmaceutically acceptable salt thereof; associated with a pharmaceutically acceptable carrier therefor.

7. A method of treating immediate hypersensitivity diseases in animals, including humans, which comprises administering to an afflicted animal a chemotherapeutically effective amount of a compound of formula (I)

(I)

wherein R$_1$ is C$_{1-4}$ alkyl and Het is a heteroaryl group selected from thienyl and thienyl substituted by from one to three groups selected from halogen and C$_{1-4}$ alkyl, or a pharmaceutically acceptable salt thereof.

* * * * *